US012590046B2

(12) United States Patent
Heins et al.

(10) Patent No.: US 12,590,046 B2
(45) Date of Patent: Mar. 31, 2026

(54) ETHYLENE RECYCLE SYSTEMS AND METHODS

(71) Applicants: Brian Heins, Humble, TX (US); Paul Hamilton, Hampshire (GB); Jason Giaquinto, Houston, TX (US); Cade Hodgson, Houston, TX (US); Heather Gilligan, Houston, TX (US)

(72) Inventors: Brian Heins, Humble, TX (US); Paul Hamilton, Hampshire (GB); Jason Giaquinto, Houston, TX (US); Cade Hodgson, Houston, TX (US); Heather Gilligan, Houston, TX (US)

(73) Assignee: ExxonMobil Chemical Patents Inc., Spring, TX (US)

( * ) Notice: Subject to any disclaimer, the term of this patent is extended or adjusted under 35 U.S.C. 154(b) by 61 days.

(21) Appl. No.: 18/577,454

(22) PCT Filed: Jun. 22, 2022

(86) PCT No.: PCT/EP2022/066957
§ 371 (c)(1),
(2) Date: Jan. 8, 2024

(87) PCT Pub. No.: WO2023/285090
PCT Pub. Date: Jan. 19, 2023

(65) Prior Publication Data
US 2024/0360054 A1      Oct. 31, 2024

Related U.S. Application Data

(60) Provisional application No. 63/221,382, filed on Jul. 13, 2021.

(30) Foreign Application Priority Data

Sep. 27, 2021    (EP) ..................................... 21199237

(51) Int. Cl.
*C07C 7/04* (2006.01)
*B01D 1/28* (2006.01)
*B01J 3/00* (2006.01)

(52) U.S. Cl.
CPC .............. *C07C 7/04* (2013.01); *B01D 1/2843* (2013.01); *B01D 1/2881* (2013.01); *B01J 3/008* (2013.01)

(58) Field of Classification Search
CPC ...... C07C 7/04; B01D 1/2843; B01D 1/2881; B01D 3/008; B01J 3/008
See application file for complete search history.

(56) References Cited

U.S. PATENT DOCUMENTS 4,218,229 A * 8/1980 Schuster ................... C07C 7/04
                                                           62/623
4,617,039 A * 10/1986 Buck ...................... F25J 3/0209
                                                           62/621
(Continued)

FOREIGN PATENT DOCUMENTS

CN       117580626 A       2/2024
WO       2023/285090 A1    1/2023

OTHER PUBLICATIONS

Extended European Search Report received for European Patent Application No. 21199237.5 mailing date Mar. 14, 2022, 6 Pages.
(Continued)

*Primary Examiner* — Ali Z Fadhel

(57) ABSTRACT

An ethylene recycle method may include: obtaining an overheads stream comprising ethylene in a first gaseous state from an ethylene purification column; heating the overheads stream in a first heat exchanger to produce a heated overheads stream comprising the ethylene in a second gaseous state; compressing the heated overheads stream to yield a compressed ethylene stream comprising the ethylene in a first supercritical state; cooling the compressed ethylene (Continued)

stream to produce a cooled, compressed ethylene stream comprising the ethylene in a first liquid state, wherein the cooling comprises passing the compressed ethylene through the first heat exchanger; reducing the pressure of the cooled, compressed ethylene stream to produce a first recycle stream comprising the ethylene in a second liquid state and optionally a third gaseous state; and introducing the first recycle stream into the ethylene purification column.

23 Claims, 4 Drawing Sheets

(56) References Cited

U.S. PATENT DOCUMENTS

| | | | | |
|---|---|---|---|---|
| 4,720,293 | A | * | 1/1988 | Rowles .................. F25J 3/0219 |
| | | | | 62/935 |
| 4,783,573 | A | | 11/1988 | Shiraki et al. |
| 4,889,545 | A | * | 12/1989 | Campbell .............. F25J 3/0242 |
| | | | | 62/621 |
| 4,966,874 | A | | 10/1990 | Young et al. |
| 5,962,761 | A | | 10/1999 | Sechrist et al. |
| 6,380,451 | B1 | | 4/2002 | Kreischer et al. |
| 6,576,721 | B2 | | 6/2003 | Kobayashi et al. |
| 8,816,147 | B2 | | 8/2014 | Vinel et al. |
| 9,012,577 | B2 | | 4/2015 | Fritz et al. |
| 2017/0081256 | A1 | | 3/2017 | Kreischer |
| 2017/0081257 | A1 | | 3/2017 | Kreischer |
| 2019/0144363 | A1 | * | 5/2019 | Hofel ...................... C07C 11/04 |
| | | | | 585/809 |
| 2020/0224968 | A1 | * | 7/2020 | Pham Duc ................ C07C 7/04 |

OTHER PUBLICATIONS

Forestière, A., (2009) "Oligomerization of monoolefins by homogeneous catalysts", Oil & Gas Science and Technology-Revue, vol. 64, No. 6, pp. 649-667. (PM).

Holden, L., (2016) "α-SABLIN™ —Full Range Linear α-Olefin Technology", CIS Petrochemicals, 4th Annual Conference, Moscow, Apr. 6-7, 2016, pp. 1-21. (PM).

Orriss, R., (2012) "Production of Ethylene ED", IP.Com Inc. 46 Pages. (EP-SR).

International Preliminary Report on Patentability received for PCT Application No. PCT/EP2022/066957, mailing date Jan. 25, 2024, 8 Pages.

International Search Report and Written Opinion received for PCT Application No. PCT/EP2022/066957, mailing date Oct. 11, 2022, 15 Pages.

Sauer, J. D. et al., (2019) "Alpha Olefins Applications Handbook chapters 2 and 3", Published by CRC Press, 24 Pages. (PM).

* cited by examiner

ETHYLENE RECYCLE SYSTEMS AND METHODS

CROSS-REFERENCE TO RELATED APPLICATIONS

This application is a National Phase Application claiming priority to PCT Application Serial No. PCT/EP2022/066957 filed Jun. 22, 2022, which claims the priority benefit of U.S. Provisional Patent Application No. 63/221,382 filed on 13 Jul. 2021 titled "Ethylene Recycle Systems And Methods" and of EP patent application Ser. No. 21/199,237.5 filed on 27 Sep. 2021 titled "Ethylene Recycle Systems And Methods", by which 63/221,382 and 21199237.5 are incorporated herein by reference in their entirety.

FIELD

The present disclosure relates to ethylene recycle systems and methods that may return unconverted ethylene to an ethylene purification column without utilizing an independent refrigeration system to cool recycle ethylene.

BACKGROUND

Low molecular weight hydrocarbons (e.g., having a carbon number of about $C_{24}$ or less) are commercially valuable compounds that may be used as starting materials in processes like polymerization or used directly for formulating lubricants. For example, linear alpha olefins (LAOs), which also may be referred to as linear alpha alkenes, linear terminal olefins, normal alpha olefins, or linear terminal alkenes, may be used, for example, as comonomers during copolymerization of ethylene, as a precursor for linear aldehydes and carboxylic acids formed through oxidation, as a precursor for linear internal olefins (LIOs) formed through double bond isomerization, and as an additive directly incorporated into drilling fluids, surfactants, lubricants, detergents, and the like, optionally after further chemical transformation thereof.

One synthetic route to afford low molecular weight hydrocarbons is ethylene oligomerization. The feed for ethylene oligomerization processes is usually high purity 'polymer' grade ethylene. For ethylene oligomerization to be economically robust, the overall ethylene conversion should be high (ideally greater than about 95 wt % conversion). To improve overall ethylene conversion, unconverted ethylene is recycled. For example, overheads from an ethylene oligomerization process may be purified before being reintroduced to the ethylene oligomerization process to achieve further reaction thereof.

Ethylene purification typically utilizes an ethylene purification column where the column overheads are high purity ethylene (in a mixed liquid and gaseous state) that needs to be re-compressed before conveyance to an ethylene oligomerization reactor. One limitation of this process is that the compressor may not intake liquid ethylene, or compressor damage and reduced compressor lifetimes may occur. To mitigate or eliminate the risk of liquid ethylene intake by the compressor in conventional ethylene purification processes, the column overheads obtained from the ethylene purification column in a mixed liquid and gaseous state are cooled with a refrigerant-based heat exchanger and then passed through a liquid knockout drum to flash the cooled ethylene. Liquid ethylene is then recycled back to the ethylene purification column and the gaseous ethylene may be heated before introduction to the compressor. This process, including the refrigeration equipment utilized therein, uses a significant amount of energy. Simpler, less costly and less energy-intensive systems and methods would be of value for promoting ethylene purification and recycling.

SUMMARY

The present disclosure relates to ethylene recycle systems and methods that may return unconverted ethylene to an ethylene purification column without utilizing an independent refrigeration system to cool recycle ethylene.

A nonlimiting example method of the present disclosure comprises: obtaining an overheads stream comprising ethylene in a first gaseous state from an ethylene purification column; heating the overheads stream in a first heat exchanger to produce a heated overheads stream comprising the ethylene in a second gaseous state; compressing the heated overheads stream to yield a compressed ethylene stream comprising the ethylene in a first supercritical state; cooling the compressed ethylene stream to produce a cooled, compressed ethylene stream comprising the ethylene in a first liquid state, wherein the cooling comprises (a) passing the compressed ethylene through a second heat exchanger and then (b) passing the compressed ethylene through the first heat exchanger, and wherein in the first heat exchanger heat flow in the first heat exchanger is from the compressed ethylene stream to the overheads stream; reducing the pressure of the cooled, compressed ethylene stream to produce a first recycle stream comprising the ethylene in a second liquid state and optionally a third gaseous state; and introducing the first recycle stream into the ethylene purification column.

Another nonlimiting example method of the present disclosure comprises: obtaining an overheads stream comprising ethylene in a first gaseous state from an ethylene purification column comprising an embedded drum in an overheads portion of the ethylene purification column; heating the overheads stream in a first heat exchanger to produce a heated overheads stream comprising the ethylene in a second gaseous state; compressing the heated overheads stream to yield a compressed ethylene stream comprising the ethylene in a first supercritical state; cooling the compressed ethylene stream to produce a cooled, compressed ethylene stream comprising the ethylene in a first liquid state; reducing the pressure of the cooled, compressed ethylene stream to produce a first recycle stream comprising the ethylene in a second liquid state and optionally a third gaseous state; and introducing the first recycle stream into the ethylene purification column.

A nonlimiting example system of the present disclosure comprises: an ethylene purification column; a first heat exchanger; a compressor; an adiabatic expansion valve or expander; an overheads line fluidly coupling an overheads portion of the ethylene purification column and the first heat exchanger; a heated overheads line fluidly coupling the first heat exchanger and the compressor; a compressed ethylene line fluidly coupling the compressor and the adiabatic expansion valve or the expander, wherein the compressed ethylene line passes through the first heat exchanger independent of the overheads line; and a recycle line fluidly coupling the adiabatic expansion valve or the expander and the ethylene purification column.

BRIEF DESCRIPTION OF THE DRAWINGS

The following figures are included to illustrate certain aspects of the disclosure, and should not be viewed as exclusive configurations. The subject matter disclosed is capable of considerable modifications, alterations, combinations, and equivalents in form and function, as will occur to one having ordinary skill in the art and having the benefit of this disclosure.

DETAILED DESCRIPTION

Figure 1:
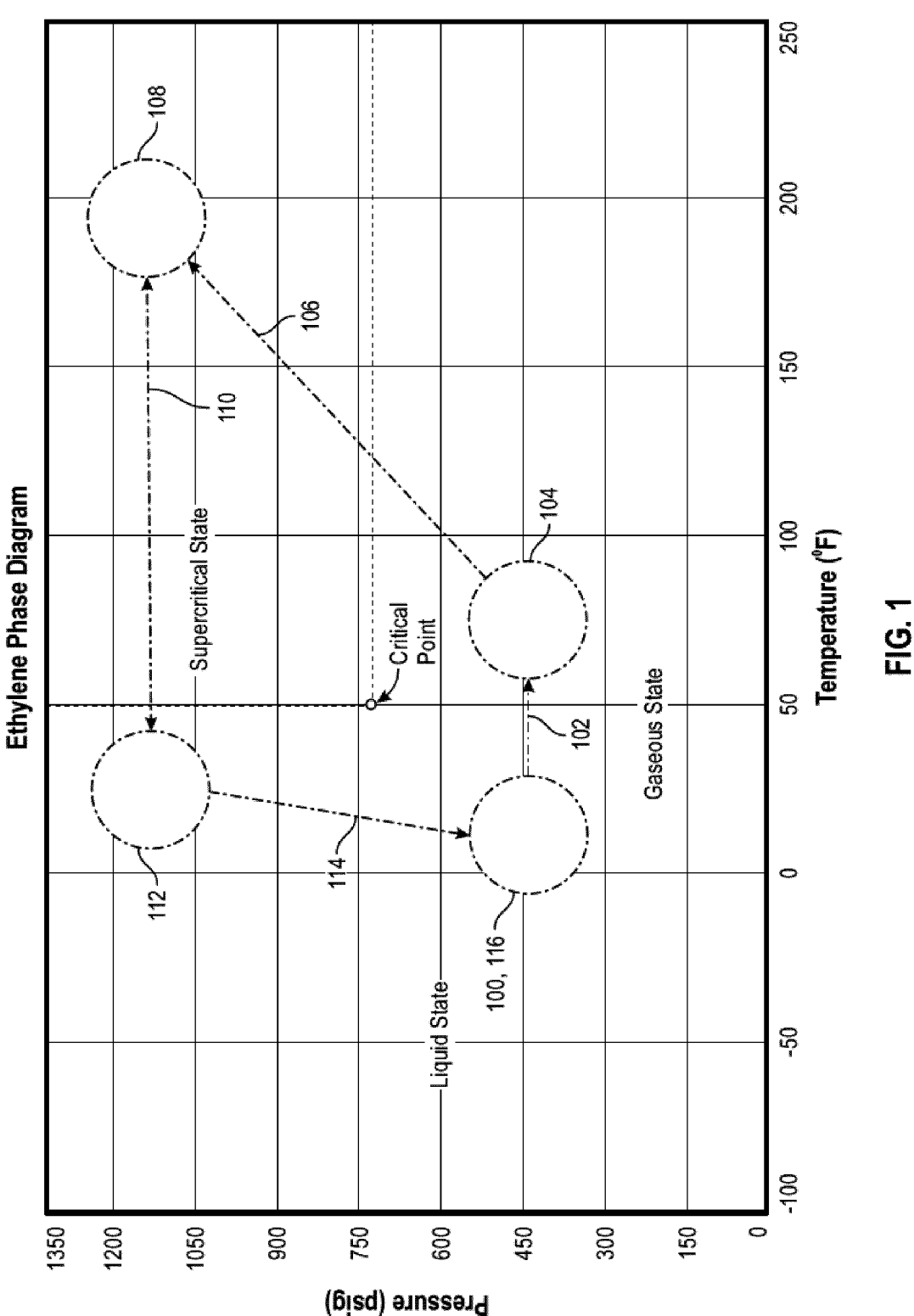
FIG. 1 illustrates a phase diagram of ethylene overlaid with a partial block diagram of a nonlimiting example method for purifying ethylene according to the present disclosure.

The present disclosure relates to ethylene recycle systems and methods that may return unconverted ethylene to an ethylene purification column without utilizing an independent refrigeration system to cool recycle ethylene. To achieve this feature, the methods and systems described herein leverage the phase behavior of ethylene, represented by the phase diagram of ethylene. That is, the temperature and pressure of various ethylene streams present throughout the recycle systems and methods disclosed herein are set to target specified regions of the ethylene phase diagram, including the region where ethylene is in a supercritical state. The terms state and phase are used synonymously and interchangeably herein. By leveraging the phase behavior of ethylene, various ethylene streams in the methods and systems described herein may be heated or cooled with limited external input. The methods and systems described herein may utilize the various ethylene streams in one or more heat exchangers, wherein heat may flow from a hotter ethylene stream to a cooler ethylene stream entering another portion of the system and method. Using heat exchange between ethylene streams having different temperatures within the methods and systems described herein in lieu of refrigeration or heaters may advantageously reduce the external enthalpy input and output needed to affect ethylene recycling, thereby making the methods and systems less energy-intensive than conventional ethylene recycle systems and methods.

Particularly advantageous configurations of the systems and methods described herein may utilize an embedded drum in the ethylene purification column. The embedded drum may decrease or eliminate liquid ethylene in the overheads stream (column overheads) passed to downstream system and method operations, similar to the function of an external flash drum in conventional ethylene recycle systems but without utilizing refrigerated cooling. Decreasing liquid ethylene in the overheads stream lessens the likelihood of introducing liquid to a compressor downstream from the ethylene purification column. Further advantageously, the embedded drum also may facilitate achieving a desired temperature and pressure of the overheads stream that allows downstream components of the systems and methods to function at temperatures and pressures that may leverage the phase behavior of ethylene more effectively at various junctures of the recycling process. Additionally, the cost to implement the embedded drum may be less than implementation of a conventional flash drum.

Advantageously, the ethylene recycle systems and methods described herein are not specific to the source of the ethylene. That is, the ethylene recycle systems and methods described herein may be used in conjunction with any process where ethylene is recycled. Examples of such processes include, but are not limited to, ethylene oligomerization processes, polymerization processes, steam cracking processes, and the like.

When discussing systems, methods, and the like herein, a stream and a line are understood have the appropriate accompanying hardware like valves, pumps, and/or gauges for conveying and/or monitoring the stream within the line and providing or conveying the stream to a desired location. Further, a line does not necessarily imply a singular tubular, pipe, or other suitable structure for conveying a stream. Rather, a line indicates a fluid connection is established between system and method components composed of one or more suitable structures for containing and conveying said stream and may include one or more tube, pipe, or other suitable structure as well as equipment like valves, heat exchangers, pumps, and the like. Additionally, two system and method components that are fluidly coupled or in fluid communication indicates that the two components are connected such that fluid can be transferred between the two where intervening valves, sensors, pumps, gauges, or other equipment may be present along said fluid communication (e.g., a line). Moreover, two systems components may be in direct fluid communication with one another or indirect fluid communication, wherein two components in indirect fluid communication may have intervening system and method components in between a first named component and a second named component.

The systems and methods of the present disclosure will now be described in further detail with reference to the drawings.

FIG. 1 illustrates a phase diagram of ethylene overlaid with a partial block diagram of a nonlimiting example method for purifying ethylene according to the present disclosure. The phase diagram is labeled with the gaseous state, the liquid state, and the supercritical state of ethylene, as well as the critical point. In the overlaid partial block diagram, circles represent example temperature and pressure ranges for various ethylene streams within the recycle method, and arrows connecting the streams represent operations taken to convert one stream to another.

In the illustrated method, an ethylene purification column produces overheads stream 100. In the illustrated temperature and pressure ranges for overheads stream 100, the temperature and pressure is preferably where the ethylene is on the phase change line between the liquid state and the gaseous state, or the ethylene is in the gaseous state alone.

Overheads stream 100 is then heated 102 to produce heated overheads stream 104 where the ethylene is in the gaseous state. The heated overheads stream 104 is then compressed 106 to produce compressed ethylene stream 108. Because heated overheads stream 104 is substantially in the gaseous state when compressed, damage to a compressor affording the compression as a result of liquid ethylene introduction is much less likely to occur. When compressed, the temperature and the pressure of heated overheads stream 104 is sufficiently increased so that compressed ethylene stream 108 is in a supercritical state. As will be discussed in more detail below, a portion of compressed ethylene stream 108 may be conveyed to an ethylene oligomerization reactor. The supercritical state of the ethylene may be particularly suitable for being conveyed to an ethylene oligomerization process taking place in the ethylene oligomerization reactor.

In the recycle method, compressed ethylene stream 108 is cooled 110 by a sufficient amount to produce a cooled, compressed ethylene stream 112 that is in a liquid state. This cooling 110 may be achieved using one or more heat exchangers. That is, while cooling 110 is illustrated as a single step, the cooling 110 may comprise multiple cooling operations.

An advantageous aspect of the systems and methods described herein is that the same heat exchanger may be utilized for (a) cooling 110 compressed ethylene stream 108 to produce cooled, compressed ethylene stream 112 and (b) heating 102 overheads stream 100 to produce heated overheads stream 104, where heat flow is from compressed ethylene stream 108 (hotter) to overheads stream 100 (cooler). By leveraging the foregoing streams within the recycle systems and methods to promote heating and cooling, the need for external heating and cooling (especially refrigerant cooling, e.g., using an independent refrigeration system) may be mitigated.

After heat exchange of overheads stream 100 occurs, the pressure of cooled, compressed ethylene stream 112 is sufficiently reduced 114 to produce recycle stream 116 that may be introduced back into the ethylene purification column. The temperature and pressure of recycle stream 116 may be such that recycle stream 116 is in a liquid phase, a gaseous phase, or in both a liquid and a gaseous phase. As described hereinbelow, recycle stream 116 may undergo further adiabatic expansion before being returned to the ethylene purification column.

Figure 2:
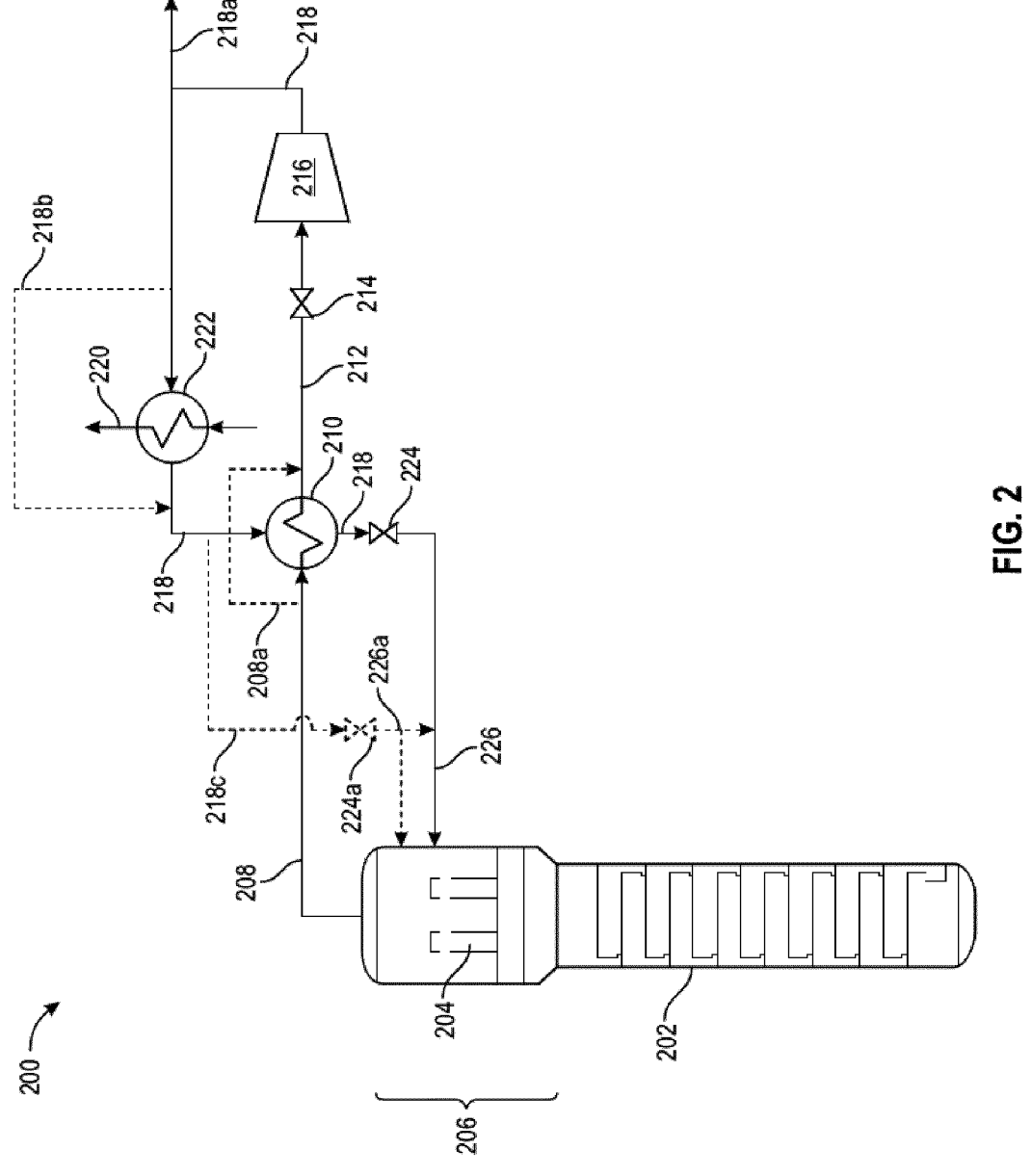
FIG. 2 illustrates a flow diagram for a nonlimiting system and method capable of recycling ethylene in an ethylene oligomerization process according to the present disclosure.

FIG. 2 illustrates a flow diagram for nonlimiting system and method 200 capable of recycling ethylene according to the present disclosure. System and method 200 includes ethylene purification column 202 that optionally includes embedded drum 204 in overheads portion 206 of ethylene purification column 202. Overheads line 208 is fluidly coupled to overheads portion 206 of ethylene purification column 202 and heat exchanger 210. Without being limited by theory, it is believed that embedded drum 204 may decrease, if not eliminate, ethylene in a liquid state in overheads line 208. The heat exchange process taking place in heat exchanger 210 is described in greater detail hereinbelow.

The illustrated system and method 200 includes said embedded drum 204. In alternative embodiments, a flash drum may be placed downstream of the ethylene purification column 202 and upstream of compressor 216 (described hereinbelow) to ensure the ethylene entering the compressor 216 is in a gaseous state. The disclosure herein relative to FIG. 1 would apply to such a system where the embedded drum is not present and the flash drum is present.

Ethylene from overheads portion 206 of ethylene purification column 202 is received by overheads line 208 and conveyed to heat exchanger 210. Ethylene received from overheads portion 206 of ethylene purification column 202 is primarily, if not completely, in a gaseous state. The ethylene in overheads line 208 at an inlet of heat exchanger 210 may have a temperature of about −30° F. to about 50° F., or about −30° F. to about 5° F., or about −10° F. to about 15° F., or about 5° F. to about 30° F., or about 15° F. to about 50° F., and a pressure of about 350 psig to about 550 psig, or about 350 psig to about 500 psig, or 450 psig to about 550 psig.

While heat exchanger 210 is illustrated as a single heat exchanger, heat exchanger 210 may comprise two or more heat exchangers in series, may comprise two or more heat exchangers in parallel, or may comprise a hybrid with three or more heat exchangers with some in parallel and some in series.

In heat exchanger 210, the ethylene is converted to a heated gaseous state. Any traces of liquid ethylene passing to heat exchanger 210 may undergo vaporization, such that substantially no liquid ethylene is passed to compressor 216. Ethylene in the heated gaseous state is conveyed from heat exchanger 210 to compressor 216 (preferably a centrifugal compressor) via heated overheads line 212 that fluidly couples heat exchanger 210 to compressor 216. The ethylene in heated overheads line 212 at an inlet of compressor 216 may have a temperature of about 50° F. to about 100° F., or about 50° F. to about 80° F., or about 60° F. to about 90° F., or about 70° F. to about 100° F., and a pressure of about 350 psig to about 550 psig, or about 350 psig to about 500 psig, or 450 psig to about 550 psig.

As discussed above, heat exchanger 210 may substantially eliminate liquid ethylene from entering heated overheads line 212, which might otherwise damage compressor 216. Advantageously, the inclusion of embedded drum 204 and heat exchanger 210 in series is believed to (a) ensure that ethylene in a liquid state does not enter compressor 216 and (b) eliminate the need for a compressor suction knockout drum that requires refrigeration. While this may be the case, other equipment may be included in system and method 200 to ensure that liquid ethylene does not enter the compressor 216.

Optionally, at least a portion of the column overheads may bypass heat exchanger 210. Illustrated in system and method 200 is optional overheads branch line 208a that bypasses heat exchanger 210 and fluidly couples overheads line 208 to heated overheads line 212. Overheads branch line 208a may allow for controlling the temperature of the gaseous ethylene in heated overheads line 212 at the inlet of compressor 216.

Also shown in system and method 200 is optional control valve 214 within heated overheads line 212 (but preferably included), for throttling the compressor stage suction in order to provide primary control of the ethylene purification column pressure.

Compressor 216 pressurizes the ethylene into a supercritical state. The supercritical ethylene at an outlet of compressor 216 may have a temperature of about 150° F. to about 250° F., or about 150° F. to about 200° F., or about 175° F. to about 225° F., or about 200° F. to about 250° F., and a pressure of about 800 psig to about 1400 psig, or about 800 psig to about 1250 psig, or 1200 psig to about 1400 psig.

The compressed ethylene exiting compressor 216 may be provided to a process that utilizes ethylene (e.g., an ethylene oligomerization process, a polymerization process, a steam cracking process, or the like). Further illustrated in system and method 200 is compressed ethylene side line 218a, through which a portion of the compressed ethylene is conveyed to an ethylene oligomerization reactor, a polymerization reactor, a steam cracking reactor, or the like. In another example, compressed ethylene side line 218a may redirect a portion of the compressed ethylene therein back to ethylene purification column 202 (fluid connection not shown). Redirection of the compressed ethylene back to ethylene purification column 202 may occur when compressor 216 is undergoing startup and/or shutdown events, for example.

Compressed ethylene not redirected to ethylene purification or provided to a process that utilizes the ethylene is then cooled in one or more heat exchangers and conveyed to adiabatic expansion valve 224 via compressed ethylene line 318. In system and method 200, cooling is achieved using heat exchangers (illustrated as two heat exchangers 210 and 222) in thermal communication with compressed ethylene line 218. The adiabatic expansion valve 224 may alternatively be an expander like a turbo-expander or an expansion turbine that expands high-pressure fluid to produce work. The work may be used to power the compressor or other component in system and method 200 or other component at the site in which the system and method 200 is located or being performed.

As illustrated in system and method 200, compressed ethylene line 218 is in thermal communication with heat exchangers 222 and 210 in series, wherein heat exchanger 210 also provides for heating of the ethylene in overheads line 208. That is, overheads line 208 and compressed ethylene line 218 pass independently through heat exchanger 210, such that heat flows from compressed ethylene to the column overheads. Heat exchange in heat exchanger 210 may convert the column overheads fully into a gaseous state, and the compressed ethylene into a liquid state. Heat exchanger 222 is upstream from heat exchanger 210 and precools the compressed ethylene before additional heat exchange takes place in heat exchanger 210. At least some of the compressed ethylene may remain in a supercritical state after passing through heat exchanger 222 before subsequently being converted to liquid ethylene in heat exchanger 210. Heat exchanger 222 may utilize any suitable cooling fluid (e.g., cooling water) supplied via cooling fluid line 220.

While heat exchanger 222 is illustrated as a single heat exchanger, heat exchanger 222 may comprise two or more heat exchangers in series, may comprise two or more heat exchangers in parallel, or may comprise a hybrid with three or more heat exchangers with some in parallel and some in series.

Optionally, a portion of the compressed ethylene may bypass the heat exchanger 222 via branch line 218_b_. Compressed ethylene transiting branch line 218_b_ may remain in a supercritical state and be recombined with compressed ethylene exiting heat exchanger 222, also in a supercritical state, which may be different than the supercritical state in branch line 218_b_. Such a bypass may be useful for controlling the temperature of ethylene purification column 202. The compressed ethylene passing through heat exchanger 222 and the compressed ethylene bypassing heat exchanger 222 may be recombined before undergoing further heat exchange in heat exchanger 210, thereby allowing the temperature, pressure and/or phase control of the compressed ethylene provided to heat exchanger 210 to be realized.

When heat exchanger 222 is present and compressed ethylene passes therethrough, the compressed ethylene at an outlet of heat exchanger 222 may have a temperature of about 75° F. to about 125° F., or about 75° F. to about 110° F., or about 100° F. to about 125° F., and a pressure of about 800 psig to about 1400 psig, or about 800 psig to about 1250 psig, or 1200 psig to about 1400 psig.

Compressed ethylene line 218 may optionally split upstream of heat exchanger 210, such that a first portion of the compressed ethylene is conveyed through heat exchanger 210 and undergo heat exchange with the overheads stream comprising gaseous ethylene and a second portion of the compressed ethylene is conveyed to adiabatic expansion valve 224_a_ (or expander) via compressed ethylene branch line 218_c_. In nonlimiting examples, adiabatic expansion valve 224_a_ may provide anti-surge control on the compressor stage and also as a minimum pressure override for overheads portion 206 of ethylene purification column 202. The compressed ethylene that reaches adiabatic expansion valve 224_a_ is substantially, if not completely, in a liquid state. The compressed ethylene that reaches adiabatic expansion valve 224_a_ may be one phase with a liquid phase or two phase with a liquid state and a supercritical state. The compressed ethylene at an inlet of adiabatic expansion valve 224_a_, if included, may have a temperature of about –10° F. to about 70° F., or about –10° F. to about 20° F., or about 0° F. to about 50° F., or about 25° F. to about 70° F., and a pressure of about 800 psig to about 1400 psig, or about 800 psig to about 1250 psig, or 1200 psig to about 1400 psig.

Other bypass configurations for this and other portions of ethylene recycling methods and systems may be included.

After exiting heat exchanger 210, the compressed ethylene that reaches adiabatic expansion valve 224 is substantially, if not completely, in a liquid state. The compressed ethylene that reaches adiabatic expansion valve 224 may be one phase with a liquid phase or two phase with a liquid state and a supercritical state. The compressed ethylene at an inlet of adiabatic expansion valve 224 may have a temperature of about –20° F. to about 50° F., or about –20° F. to about 10° F., or about 0° F. to about 30° F., or about 10° F. to about 50° F., and a pressure of about 800 psig to about 1400 psig, or about 800 psig to about 1250 psig, or 1200 psig to about 1400 psig.

Adiabatic expansion valve 224 and adiabatic expansion valve 224_a_, if included, may utilize the Joule-Thompson effect to decrease the pressure of the compressed ethylene and convert at least some of the ethylene from a liquid state to a gaseous state. That is, after the adiabatic expansion valve 224 and adiabatic expansion valve 224_a_, if included, the ethylene may be in one phase with a gaseous state or two phase with a gaseous state and a liquid state. Ethylene exiting adiabatic expansion valve 224 is conveyed to ethylene purification column 202 via recycle line 226 that fluidly couples adiabatic expansion valve 224 to ethylene purification column 202. When adiabatic expansion valve 224_a_ is included, the corresponding ethylene may be conveyed from adiabatic expansion valve 224_a_ via recycle line 226_a_ to (a) recycle line 226 and/or (b) ethylene purification column 202. Recycle line 226 and/or recycle line 226_a_ may be configured to introduce the ethylene back into ethylene purification column 202 in overheads portion 206 of ethylene purification column 202.

Depending on the temperature and pressure conditions, the ethylene introduced to ethylene purification column 202 may be in one phase with a gaseous state, one phase with a liquid state, or two phase with a gaseous state and a liquid state. The ethylene introduced to ethylene purification column 202 via recycle line 226 (and/or recycle line 226_a_, if included) at an inlet of ethylene purification column 202 may have a temperature of about –20° F. to about 20° F., or about –20° F. to about 0° F., or about –10° F. to about 10° F., or about 0° F. to about 20° F., and a pressure of about 350 psig to about 550 psig, or about 350 psig to about 425 psig, or 400 psig to about 550 psig. Typically, the overheads stream 208 is at a lower pressure than the recycle line 226 (and/or recycle line 226_a_, if included).

Therefore, some configurations of the present disclosure may feature ethylene purification systems comprising: an ethylene purification column with an embedded drum in an overheads portion of the ethylene purification column; a heat exchanger; a compressor; an adiabatic expansion valve (or expander); an overheads line fluidly coupling the overheads portion of the ethylene purification column and the heat exchanger; a heated overheads line fluidly coupling the heat exchanger and the compressor; a compressed ethylene line fluidly coupling the compressor and the adiabatic expansion valve (or expander); and a recycle line fluidly coupling the adiabatic expansion valve (or expander) and the ethylene purification column. The compressed ethylene line passes through the heat exchanger independent of the overheads line, such that heat exchange may occur between the overheads stream and the compressed ethylene stream.

Some configurations of the present disclosure may feature ethylene purification systems comprising: an ethylene purification column with an embedded drum in an overheads portion of the ethylene purification column; a first heat exchanger; a compressor; a second heat exchanger; an adiabatic expansion valve (or expander); an overheads line fluidly coupling the overheads portion of the ethylene purification column and the first heat exchanger; a heated overheads line fluidly coupling the first heat exchanger and the compressor; a compressed ethylene line fluidly coupling the compressor and the adiabatic expansion valve (or expander); and a recycle line fluidly coupling the adiabatic expansion valve (or expander) and the ethylene purification column. The compressed ethylene line passes through the second heat exchanger, such that heat exchange does not occur directly between the overheads stream and the compressed ethylene stream, and heat exchange for these two streams occur separately in the first and second heat exchangers, respectively. Optionally, a third heat exchanger may intercede in the compressed ethylene line upstream of the second heat exchanger, such that cooled, compressed ethylene is provided to the second heat exchanger.

Still other configurations of the present disclosure may feature ethylene purification systems comprising: an ethylene purification column with an embedded drum in an overheads portion of the ethylene purification column; a first heat exchanger; a compressor; a second heat exchanger; an adiabatic expansion valve (or expander); an overheads line fluidly coupling the overheads portion of the ethylene purification column and the first heat exchanger; a heated overheads line fluidly coupling the first heat exchanger and the compressor; a compressed ethylene line fluidly coupling the compressor and the adiabatic expansion valve (or expander); and a recycle line fluidly coupling the adiabatic expansion valve (or expander) and the ethylene purification column. The compressed ethylene line passes first through the second heat exchanger and then through the first heat exchanger independent of the overheads line. A cooled, compressed ethylene stream is produced by the second heat exchanger. Heat exchange may occur between the overheads stream and the cooled, compressed ethylene stream in the first heat exchanger.

Still other configurations of the present disclosure may feature ethylene purification systems comprising: an ethylene purification column; a first heat exchanger; a compressor; an adiabatic expansion valve or expander; an overheads line fluidly coupling an overheads portion of the ethylene purification column and the first heat exchanger; a heated overheads line fluidly coupling the first heat exchanger and the compressor; a compressed ethylene line fluidly coupling the compressor and the adiabatic expansion valve or the expander, wherein the compressed ethylene line passes through the first heat exchanger independent of the overheads line; and a recycle line fluidly coupling the adiabatic expansion valve or the expander and the ethylene purification column.

Optional components of the foregoing ethylene purification system configurations are described elsewhere herein. Such optional components may be present singularly or in any combination with one another in the various ethylene purification system configurations.

Figure 3:
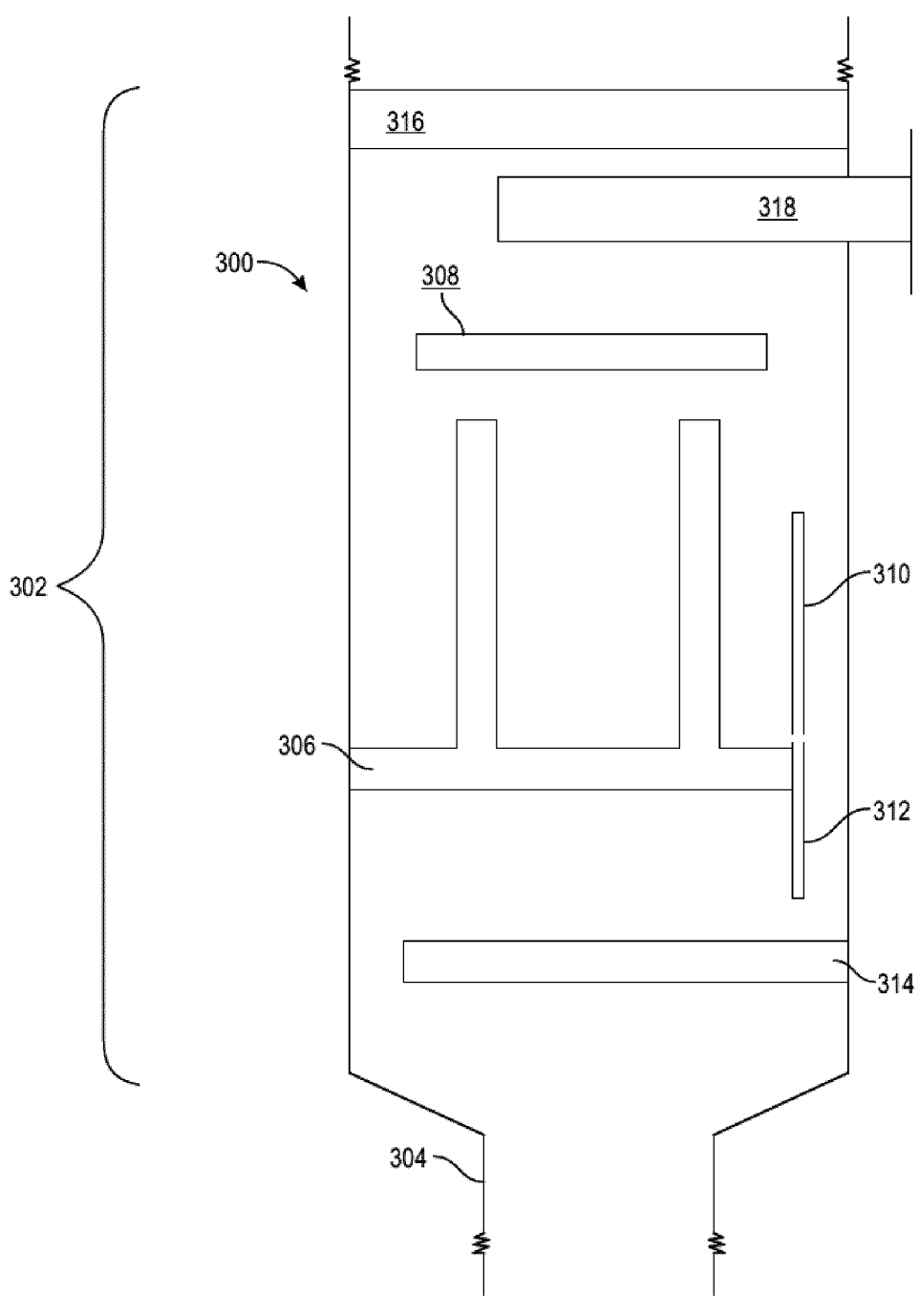
FIG. 3 illustrates a cross-sectional diagram of an embedded drum incorporated into an overheads portion of an ethylene purification column.

FIG. 3 illustrates a cross-sectional diagram of embedded drum 300 incorporated into overheads portion 302 of ethylene purification column 304. Embedded drum 300 includes chimney tray 306 with chimney tray hat 308, and overflow weir 310. The illustrated overflow weir 310 includes a drain hole (not labeled) near chimney tray 306. Extending down from chimney tray 306 is downcomer 312.

While overflow weir 310 and downcomer 312 are illustrated as a single structure that extends above and below the base of chimney tray 306, overflow weir 310 and downcomer 312 may be separate structures that extend upward from the base of chimney tray 306 toward chimney tray hat 208 and extend downward from the base of chimney tray 306 toward top tray 314, respectively, at any suitable angle (as illustrated each extending from the chimney tray 306 at a 900 angle). Above chimney tray hat 308 of embedded drum 300 is demister pad 316. Between demister pad 316 and chimney tray hat 308 is inlet 318 for a recycle line for introducing recycle ethylene. Inlet 318 may include a sparger where ethylene from the recycle line is introduced into ethylene purification column 304. Without being limited by theory, it is believed that the liquid portion of the ethylene will fall onto chimney tray hat 308 and continue down to chimney tray 306 while gaseous ethylene (if any) will rise through demister pad 316 and to an overheads line. In an alternative configuration, the inlet (e.g., a sparger) may be between the chimney tray and chimney tray and extend any suitable distance into the overheads portion of ethylene purification column. In such configurations, the inlet may be positioned to allow the liquid ethylene to collect in the chimney tray, pass through the drain hole in the overflow weir, flow to the top tray 314, or a combination of two or more of the foregoing.

FIG. 3 is a nonlimiting example of an embedded drum. Alternative configurations may also be suitable including configurations without the overflow weir, configurations with the downcomer not attached to the chimney tray, and combinations thereof. Further, other configurations suitable for achieving a reflux stream return mechanism in the overheads portion of ethylene purification column are suitable.

Figure 4:
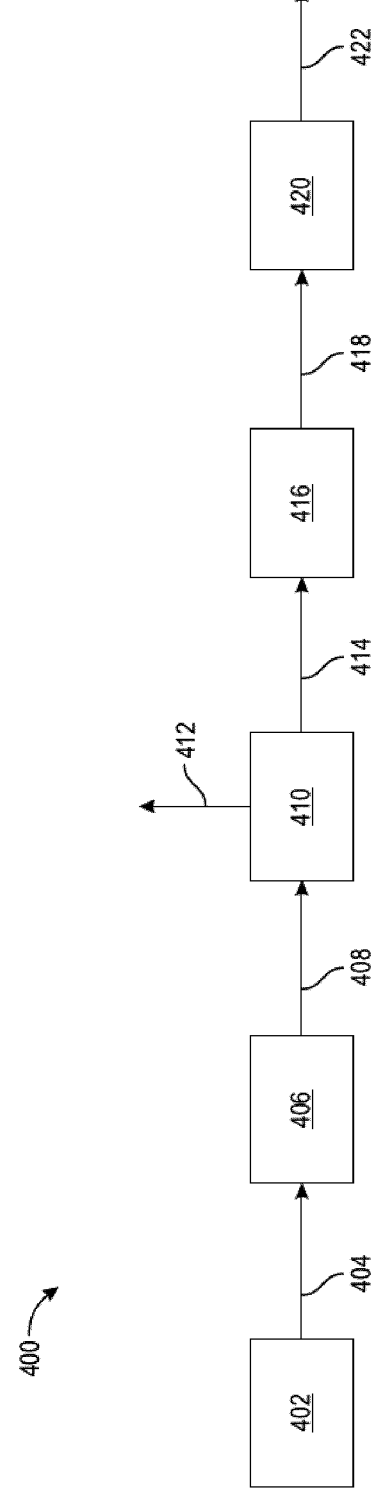
FIG. 4 illustrates a flow diagram of a nonlimiting example of an ethylene recycling method of the present disclosure.

FIG. 4 illustrates a flow diagram of a nonlimiting example of an ethylene recycling method of the present disclosure. In method 400, overheads stream 402 is obtained from ethylene purification column (e.g., from ethylene purification column 202 via overheads line 208 of FIG. 2). By virtue of the embedded drum in the ethylene purification column, overheads stream 402 may comprise substantially ethylene, if not completely, in a gaseous state. The ethylene in overheads stream 402 prior to heating 404 may have a temperature of about −30° F. to about 50° F., or about −30° F. to about 5° F., or about −10° F. to about 15° F., or about 5° F. to about 30° F., or about 15° F. to about 50° F., and a pressure of about 350 psig to about 550 psig, or about 350 psig to about 500 psig, or 450 psig to about 550 psig. Any residual liquid ethylene in overheads stream 402 may be addressed subsequently.

Overheads stream 402 undergoes heating 404 to produce heated overheads stream 406. Heating 404 may be accomplished with a heat exchanger (e.g., heat exchanger 210 of FIG. 2). In addition to reaching a desired temperature for subsequent compression 408, heating 404 may convert residual liquid ethylene in overheads stream 402 substantially into a gaseous state in heated overheads stream 406.

As described above in reference to FIG. 2, overheads stream 402 may be split such that a portion of overheads stream 402 undergoes heating 404 and another portion of overheads stream 402 is not heated and bypasses the heating equipment (heat exchanger). The two portions may be recombined downstream of the heating equipment. The degree to which overheads stream 402 is split between the two portions (heating and not heating) may regulate the temperature of resultant heated overheads stream 406 and/or cooled, compressed ethylene stream 416 described below. With or without splitting of overheads stream 402, heated overheads stream 406 may have a temperature of about 50° F. to about 100° F., or about 50° F. to about 80° F., or about 60° F. to about 90° F., or about 70° F. to about 100° F., and a pressure of about 350 psig to about 550 psig, or about 350 psig to about 500 psig, or 450 psig to about 550 psig.

Heated overheads stream 406 then undergoes compression 408 to produce compressed ethylene stream 410. Preferably, during compression 408, the ethylene of heated overheads stream 406 is converted to a supercritical state in compressed ethylene stream 410. Compression 408 may be achieved with a compressor, preferably a centrifugal compressor, (e.g., compressor 216 of FIG. 2). After compression 408, compressed ethylene stream 410 may have a temperature of about 150° F. to about 250° F., or about 150° F. to about 200° F., or about 175° F. to about 225° F., or about 200° F. to about 250° F., and a pressure of about 800 psig to about 1400 psig, or about 800 psig to about 1250 psig, or 1200 psig to about 1400 psig.

A portion of the compressed ethylene stream 410 may be conveyed 412 to an ethylene oligomerization reactor or process or returned to the ethylene purification column as described above in reference to FIG. 2.

A portion of compressed ethylene stream 410 may then undergo cooling 414 to produce cooled, compressed ethylene stream 416. Cooling 414 may be achieved by passing compressed ethylene stream 410 through one or more heat exchangers (e.g., heat exchanger 210 and/or heat exchanger 222 of FIG. 2, preferably both heat exchanger 222 and heat exchanger 210). For example, cooling 414 may include passing at least a portion of compressed ethylene stream 410 through a heat exchanger chilled by a cooling fluid, such as chilled water (e.g., heat exchanger 222 of FIG. 3) and then through the heat exchanger providing heating 404 to overheads stream 402 (e.g., heat exchanger 210 of FIG. 2). In another example, cooling 414 may include passing compressed ethylene stream 410 through a single heat exchanger (e.g., heat exchanger 210 of FIG. 2) where the heat exchanger is the single heat exchanger providing heating 404 to overheads stream 402.

When multiple heat exchangers are used, the ethylene obtained after initial cooling (e.g., in a heat exchanger chilled by a cooling fluid such as chilled water) may have an intermediate temperature and pressure relative to cooled, compressed ethylene stream 416 that is subsequently obtained. At an intermediate degree of cooling (e.g., at a location between the heat exchangers), the ethylene may still be in a supercritical state, and have a temperature of about 75° F. to about 125° F., or about 75° F. to about 110° F., or about 100° F. to about 125° F., and a pressure of about 800 psig to about 1400 psig, or about 800 psig to about 1250 psig, or 1200 psig to about 1400 psig. Upon the completion of cooling 414, cooled, compressed ethylene stream 416 may be substantially, if not completely, in a liquid state. For example, cooled, compressed ethylene stream 416 may be in a single phase with a liquid state or two phases with a liquid state and a supercritical state. Cooled, compressed ethylene stream may have a temperature of about −10° F. to about 50° F., or about −10° F. to about 10° F., or about 0° F. to about 30° F., or about 10° F. to about 50° F., and a pressure of about 800 psig to about 1400 psig, or about 800 psig to about 1250 psig, or 1200 psig to about 1400 psig.

Cooled, compressed ethylene stream 416 then undergoes pressure reduction 418 to produce recycle stream 420 that is introduced 422 to the ethylene purification column. Pressure reduction 418 may be achieved with an adiabatic expansion valve (e.g., adiabatic expansion valve 224 of FIG. 2) or expander to produce recycle stream 420. The ethylene that is introduced to the ethylene purification column may be one phase with a gaseous state, one phase with a liquid state, or two phase with a gaseous state and a liquid state. Depending on the temperature and pressure conditions, the ethylene in recycle stream 420 may be partially in the gaseous state and partially in the liquid state. The ethylene in recycle stream 420 at an inlet of the ethylene purification column may have a temperature of about −20° F. to about 20° F., or about −20° F. to about 0° F., or about −10° F. to about 10° F., or about 0° F. to about 20° F., and a pressure of about 300 psig to about 500 psig or about 300 psig to about 425 psig, or 400 psig to about 500 psig.

Compressed ethylene stream 410 at an intermediate degree of cooling between heat exchangers may be split (e.g., as described in reference to FIG. 2), such that a portion thereof continues cooling in a second heat exchanger, as described above, and another portion bypasses further active cooling and is reduced in pressure (e.g., using adiabatic expansion valve 224a of FIG. 2) or expander to produce a second recycle stream. The second recycle stream may be combined with the recycle stream 420 or be introduced separately into the ethylene purification column.

Accordingly, methods of the present disclosure may comprise: obtaining an overheads stream from an ethylene purification column; heating the overheads stream to produce a heated overheads stream; compressing the heated overheads stream to yield a compressed ethylene stream; cooling the compressed ethylene stream to produce a cooled, compressed ethylene stream; reducing a pressure of the cooled, compressed ethylene stream to produce a recycle stream; and introducing the recycle stream into the ethylene purification column. The overheads stream may comprise ethylene in a first gaseous state and be obtained from an embedded drum in an overheads portion of the ethylene purification column. The heated overheads stream may comprise substantially gaseous ethylene in a second gaseous state. The compressed ethylene stream may comprise ethylene in a first supercritical state. The cooled, compressed ethylene stream may comprise ethylene in a first liquid state. Optionally, the compressed ethylene stream may be cooled to an intermediate state, which is a second supercritical state, before further cooling to afford the cooled, compressed ethylene stream. The recycle stream may comprise ethylene in a second liquid state, optionally in combination with a third gaseous state. Preferably, the overheads stream and the compressed ethylene stream pass through a heat exchanger, wherein the compressed ethylene stream heats the overheads stream. More preferably, the compressed ethylene stream is cooled to a second supercritical state in a heat exchanger chilled with a cooling fluid prior to being conveyed to a heat exchanger through which the overheads stream also passes.

Various aspects of the systems and methods described herein may utilize computer systems, such as to process data received within the systems and methods to determine operational parameters of the ethylene recycle process. Such systems and methods may include a non-transitory computer readable medium containing instructions that, when implemented, cause one or more processors to carry out the methods described herein.

"Computer-readable medium" or "non-transitory, computer-readable medium," as used herein, refers to any non-transitory storage and/or transmission medium that participates in providing instructions to a processor for execution. Such a medium may include, but is not limited to, non-volatile media and volatile media. Non-volatile media includes, for example, NVRAM, or magnetic or optical disks. Volatile media includes dynamic memory, such as main memory. Common forms of computer-readable media include, for example, a floppy disk, a flexible disk, a hard disk, an array of hard disks, a magnetic tape, or any other magnetic medium, magneto-optical medium, a CD-ROM, a holographic medium, any other optical medium, a RAM, a PROM, and EPROM, a FLASH-EPROM, a solid state medium like a memory card, any other memory chip or cartridge, or any other tangible medium from which a computer can read data or instructions. When the computer-readable media is configured as a database, it is to be understood that the database may be any type of database, such as relational, hierarchical, object-oriented, and/or the like. Accordingly, exemplary embodiments of the present systems and methods may be considered to include a tangible storage medium or tangible distribution medium and art-recognized equivalents and successor media, in which the software implementations embodying the present techniques are stored.

The methods described herein can be performed using computing devices or processor-based devices that include a processor; a memory coupled to the processor; and instructions provided to the memory, wherein the instructions are executable by the processor to perform the methods described herein. The instructions can be a portion of code on a non-transitory computer readable medium. Any suitable processor-based device may be utilized for implementing all or a portion of embodiments of the present techniques, including without limitation personal computers, networks of personal computers, laptop computers, computer workstations, mobile devices, multi-processor servers or workstations with (or without) shared memory, high performance computers, and the like. Moreover, embodiments may be implemented on application specific integrated circuits (ASICs) or very large scale integrated (VLSI) circuits.

For example, the methods and systems of the present disclosure may incorporate a controller capable of receiving data from various sensors in the system and communicating instructions regarding operational parameters to equipment associated with the system. The instructions may, for example, relate to (a) the relative flow rates or mass flow rates to be implemented at the various locations where streams and/or lines may split and/or (b) suction and discharge pressures of the compression stage.

EXAMPLE EMBODIMENTS

Embodiment 1. A method comprising: obtaining an overheads stream comprising ethylene in a first gaseous state from an ethylene purification column; heating the overheads stream in a first heat exchanger to produce a heated overheads stream comprising the ethylene in a second gaseous state; compressing the heated overheads stream to yield a compressed ethylene stream comprising the ethylene in a first supercritical state; cooling the compressed ethylene stream to produce a cooled, compressed ethylene stream comprising the ethylene in a first liquid state, wherein the cooling comprises (a) passing the compressed ethylene through a second heat exchanger and then (b) passing the compressed ethylene through the first heat exchanger, and wherein in the first heat exchanger heat flow in the first heat exchanger is from the compressed ethylene stream to the overheads stream; reducing the pressure of the cooled, compressed ethylene stream to produce a first recycle stream comprising the ethylene in a second liquid state and optionally a third gaseous state; and introducing the first recycle stream into the ethylene purification column.

Embodiment 2. The method of Embodiment 1, wherein the ethylene purification column comprises an embedded drum in an overheads portion of the ethylene purification column.

Embodiment 3. The method of Embodiment 1 or Embodiment 2, further comprising: splitting the overheads stream into at least two portions; heating a first portion of the overheads stream in the first heat exchanger; conveying a second portion of the overheads stream to bypass the first heat exchanger; and combining the first and second portions of the overheads stream after passing the first portion through the first heat exchanger to produce the heated overheads stream.

Embodiment 4. The method of any of Embodiments 1-3, further comprising: conveying a portion of the compressed ethylene stream to an ethylene oligomerization reactor, a polymerization reactor, or a steam cracking reactor.

Embodiment 5. The method of any of Embodiments 1-4, wherein the passing of the compressed ethylene stream through the second heat exchanger places the compressed ethylene in a second supercritical state.

Embodiment 6. The method of any of Embodiments 1-5, further comprising: splitting the compressed ethylene stream between the first and second heat exchangers into at least two portions; further cooling a first portion of the at least two portions in the first heat exchanger; conveying a second portion of the at least two portions to bypass the first heat exchanger; and combining the first and second portions of the at least two portions after passing the first portion through the first heat exchanger to produce the cooled, compressed ethylene stream.

Embodiment 7. The method of any of Embodiments 1-6 further comprising: splitting the compressed ethylene stream between the first and second heat exchangers into at least two portions; further cooling a first portion of the at least two portions in the first heat exchanger; and reducing pressure of a second portion of the at least two portions without passing the second portion through the first heat exchanger to produce a second recycle stream.

Embodiment 8. The method of Embodiment 7 further comprising: optionally, combining the second recycle stream with the first recycle stream before introducing the first recycle stream to the ethylene purification column; and introducing the second recycle stream to the ethylene purification column.

Embodiment 9. The method of any of Embodiments 1-8, wherein the first recycle stream is introduced into the overheads portion of the ethylene purification column.

Embodiment 10. The method of any of Embodiments 1-9, wherein the overheads stream is at a temperature of about −30° F. to about 50° F. and a pressure of about 350 psig to about 550 psig.

Embodiment 11. The method of any of Embodiments 1-10, wherein the heated overheads stream is at a temperature of about 50° F. to about 100° F. and a pressure of about 350 psig to about 550 psig.

Embodiment 12. The method of any of Embodiments 1-11, wherein the heated overheads stream is compressed with a centrifugal compressor.

Embodiment 13. The method of any of Embodiments 1-12, wherein, after compressing, the compressed ethylene stream is at a temperature of about 150° F. to about 250° F. and a pressure of about 800 psig to about 1400 psig.

Embodiment 14. The method of any of Embodiments 1-13, wherein the cooled, compressed ethylene stream is at a temperature of about −10° F. to about 50° F. and a pressure of about 800 psig to about 1400 psig.

Embodiment 15. The method of any of Embodiments 1-14, wherein the recycle stream is at a temperature of about −20° F. to about 20° F. and a pressure of about 300 psig to about 500 psig.

Embodiment 16. The method of any of Embodiments 1-15, wherein the cooling of the compressed ethylene stream does not utilize refrigeration.

Embodiment 17. A method comprising: obtaining an overheads stream comprising ethylene in a first gaseous state from an ethylene purification column comprising an embedded drum in an overheads portion of the ethylene purification column; heating the overheads stream in a first heat exchanger to produce a heated overheads stream comprising the ethylene in a second gaseous state; compressing the heated overheads stream to yield a compressed ethylene stream comprising the ethylene in a first supercritical state; cooling the compressed ethylene stream to produce a cooled, compressed ethylene stream comprising the ethylene in a first liquid state; reducing the pressure of the cooled, compressed ethylene stream to produce a first recycle stream comprising the ethylene in a second liquid state and optionally a third gaseous state; and introducing the first recycle stream into the ethylene purification column.

Embodiment 18. The method of Embodiment 17, further comprising: splitting the overheads stream into at least two portions; heating a first portion of the overheads stream in the first heat exchanger; conveying a second portion of the overheads stream to bypass the first heat exchanger; and combining the first and second portions of the overheads stream after passing the first portion through the first heat exchanger to produce the heated overheads stream.

Embodiment 19. The method of any of Embodiments 17-18, further comprising: conveying a portion of the compressed ethylene stream to an ethylene oligomerization reactor, a polymerization reactor, or a steam cracking reactor.

Embodiment 20. The method of any of Embodiments 17-19, wherein the passing of the compressed ethylene stream through the second heat exchanger places the compressed ethylene in a second supercritical state.

Embodiment 21. The method of any of Embodiments 17-20, further comprising: splitting the compressed ethylene stream between the first and second heat exchangers into at least two portions; further cooling a first portion of the at least two portions in the first heat exchanger; conveying a second portion of the at least two portions to bypass the first heat exchanger; and combining the first and second portions of the at least two portions after passing the first portion through the first heat exchanger to produce the cooled, compressed ethylene stream.

Embodiment 22. The method of any of Embodiments 17-21 further comprising: splitting the compressed ethylene stream between the first and second heat exchangers into at least two portions; further cooling a first portion of the at least two portions in the first heat exchanger; and reducing pressure of a second portion of the at least two portions without passing the second portion through the first heat exchanger to produce a second recycle stream.

Embodiment 23. The method of Embodiment 22 further comprising: optionally, combining the second recycle stream with the first recycle stream before introducing the first recycle stream to the ethylene purification column; and introducing the second recycle stream to the ethylene purification column.

Embodiment 24. The method of any of Embodiments 17-23, wherein the first recycle stream is introduced into the overheads portion of the ethylene purification column.

Embodiment 25. The method of any of Embodiments 17-24, wherein the overheads stream is at a temperature of about −30° F. to about 50° F. and a pressure of about 350 psig to about 550 psig.

Embodiment 26. The method of any of Embodiments 17-25, wherein the heated overheads stream is at a temperature of about 50° F. to about 100° F. and a pressure of about 350 psig to about 550 psig.

Embodiment 27. The method of any of Embodiments 17-26, wherein the heated overheads stream is compressed with a centrifugal compressor.

Embodiment 28. The method of any of Embodiments 17-27, wherein, after compressing, the compressed ethylene stream is at a temperature of about 150° F. to about 250° F. and a pressure of about 800 psig to about 1400 psig.

Embodiment 29. The method of any of Embodiments 17-28, wherein the cooled, compressed ethylene stream is at a temperature of about −10° F. to about 50° F. and a pressure of about 800 psig to about 1400 psig.

Embodiment 30. The method of any of Embodiments 17-29, wherein the recycle stream is at a temperature of about −20° F. to about 20° F. and a pressure of about 300 psig to about 500 psig.

Embodiment 31. The method of any of Embodiments 17-30, wherein the cooling of the compressed ethylene stream does not utilize refrigeration.

Embodiment 32. A system comprising: an ethylene purification column; a first heat exchanger; a compressor; an adiabatic expansion valve or expander; an overheads line fluidly coupling an overheads portion of the ethylene purification column and the first heat exchanger; a heated overheads line fluidly coupling the first heat exchanger and the compressor; a compressed ethylene line fluidly coupling the compressor and the adiabatic expansion valve or the expander, wherein the compressed ethylene line passes through the first heat exchanger independent of the overheads line; and a recycle line fluidly coupling the adiabatic expansion valve or the expander and the ethylene purification column.

Embodiment 33. The system of embodiment 32, wherein the ethylene purification column comprises an embedded drum in an overheads portion of the ethylene purification column.

Embodiment 34. The system of any of Embodiments 32-33, further comprising: a second heat exchanger chilled with a cooling fluid, the compressed ethylene line passing through the second heat exchanger before passing through the first heat exchanger.

Embodiment 35. The system of any of Embodiments 32-34, further comprising: a compressed ethylene split line fluidly coupling the compressor and an ethylene oligomerization reactor, a polymerization reactor, or a steam cracking reactor.

Embodiment 36. The system of any of Embodiments 32-35, wherein the compressor is a centrifugal compressor.

Embodiment 37. The system of any of Embodiments 32-36, further comprising: a controller capable of receiving data from the system and sending instructions regarding one or more operational parameters to the system.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the incarnations of the present inventions. At the very least, and not as an attempt to limit the application of the doctrine of equivalents to the scope of the claim, each numerical parameter should at least be construed in light of the number of reported significant digits and by applying ordinary rounding techniques.

One or more illustrative incarnations incorporating one or more invention elements are presented herein. Not all features of a physical implementation are described or shown in this application for the sake of clarity. It is understood that in the development of a physical embodiment incorporating one or more elements of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

Therefore, the present invention is well adapted to attain the ends and advantages mentioned as well as those that are inherent therein. The particular examples and configurations disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative examples disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:

obtaining an overheads stream comprising ethylene in a first gaseous state from an ethylene purification column;

heating the overheads stream in a first heat exchanger to produce a heated overheads stream comprising the ethylene in a second gaseous state;

compressing the heated overheads stream to yield a compressed ethylene stream comprising the ethylene in a first supercritical state;

cooling the compressed ethylene stream to produce a cooled, compressed ethylene stream comprising the ethylene in a first liquid state, wherein the cooling comprises (a) passing the compressed ethylene through a second heat exchanger and then (b) passing the compressed ethylene through the first heat exchanger, and wherein in the first heat exchanger heat flow in the first heat exchanger is from the compressed ethylene stream to the overheads stream;

reducing the pressure of the cooled, compressed ethylene stream to produce a first recycle stream comprising the ethylene in a second liquid state and optionally a third gaseous state; and introducing the first recycle stream into the ethylene purification column.

2. The method of claim 1, wherein the ethylene purification column comprises an embedded drum in an overheads portion of the ethylene purification column.

3. The method of claim 1, further comprising:

splitting the overheads stream into at least two portions;

heating a first portion of the overheads stream in the first heat exchanger;

conveying a second portion of the overheads stream to bypass the first heat exchanger; and combining the first and second portions of the overheads stream after passing the first portion through the first heat exchanger to produce the heated overheads stream.

4. The method of claim 1, further comprising:

conveying a portion of the compressed ethylene stream to an ethylene oligomerization reactor, a polymerization reactor, or a steam cracking reactor.

5. The method of claim 1, wherein the passing of the compressed ethylene stream through the second heat exchanger places the compressed ethylene in a second supercritical state.

6. The method of claim 1, further comprising:

splitting the compressed ethylene stream between the first and second heat exchangers into at least two portions;

further cooling a first portion of the at least two portions in the first heat exchanger;

conveying a second portion of the at least two portions to bypass the first heat exchanger; and combining the first and second portions of the at least two portions after passing the first portion through the first heat exchanger to produce the cooled, compressed ethylene stream.

7. The method of claim 1, further comprising:

splitting the compressed ethylene stream between the first and second heat exchangers into at least two portions;

further cooling a first portion of the at least two portions in the first heat exchanger; and reducing pressure of a second portion of the at least two portions without passing the second portion through the first heat exchanger to produce a second recycle stream.

8. The method of claim 7 further comprising:

optionally, combining the second recycle stream with the first recycle stream before introducing the first recycle stream to the ethylene purification column; and introducing the second recycle stream to the ethylene purification column.

9. The method of claim 1, wherein the first recycle stream is introduced into the overheads portion of the ethylene purification column.

10. The method of claim 1, wherein the overheads stream is at a temperature of about –30° F. to about 50° F. and a pressure of about 350 psig to about 550 psig.

11. The method of claim 1, wherein the heated overheads stream is at a temperature of about 50° F. to about 100° F. and a pressure of about 350 psig to about 550 psig.

12. The method of claim 1, wherein the heated overheads stream is compressed with a centrifugal compressor.

13. The method of claim 1, wherein, after compressing, the compressed ethylene stream is at a temperature of about 150° F. to about 250° F. and a pressure of about 800 psig to about 1400 psig.

14. The method of claim 1, wherein the cooled, compressed ethylene stream is at a temperature of about –10° F. to about 50° F. and a pressure of about 800 psig to about 1400 psig.

15. The method of claim 1, wherein the recycle stream is at a temperature of about –20° F. to about 20° F. and a pressure of about 300 psig to about 500 psig.

16. The method of claim 1, wherein the cooling of the compressed ethylene stream does not utilize refrigeration.

17. A method comprising:

obtaining an overheads stream comprising ethylene in a first gaseous state from an ethylene purification column comprising an embedded drum in an overheads portion of the ethylene purification column;

heating the overheads stream in a first heat exchanger to produce a heated overheads stream comprising the ethylene in a second gaseous state;

compressing the heated overheads stream to yield a compressed ethylene stream comprising the ethylene in a first supercritical state;

cooling the compressed ethylene stream to produce a cooled, compressed ethylene stream comprising the ethylene in a first liquid state;

reducing the pressure of the cooled, compressed ethylene stream to produce a first recycle stream comprising the ethylene in a second liquid state and optionally a third gaseous state; and introducing the first recycle stream into the ethylene purification column.

18. A system comprising:

an ethylene purification column;

a first heat exchanger;

a compressor;

an adiabatic expansion valve or expander;

an overheads line fluidly coupling an overheads portion of the ethylene purification column and the first heat exchanger;

a heated overheads line fluidly coupling the first heat exchanger and the compressor;

a compressed ethylene line fluidly coupling the compressor and the adiabatic expansion valve or the expander, wherein the compressed ethylene line passes through the first heat exchanger independent of the overheads line; and a recycle line fluidly coupling the adiabatic expansion valve or the expander and the ethylene purification column.

19. The system of claim 18, wherein the ethylene purification column comprises an embedded drum in an overheads portion of the ethylene purification column.

20. The system of claim 18, further comprising:

a second heat exchanger chilled with a cooling fluid, the compressed ethylene line passing through the second heat exchanger before passing through the first heat exchanger.

21. The system of claim 18, further comprising:

a compressed ethylene split line fluidly coupling the compressor and an ethylene oligomerization reactor, a polymerization reactor, or a steam cracking reactor.

22. The system of claim 18, wherein the compressor is a centrifugal compressor.

23. The system of claim 18, further comprising:

a controller capable of receiving data from the system and sending instructions regarding one or more operational parameters to the system.

* * * * *